United States Patent [19]

Lee

[11] Patent Number: 5,365,925
[45] Date of Patent: Nov. 22, 1994

[54] DISPOSABLE CALIBRATION BOOT FOR MULTI-POINT CALIBRATION IN FIBER OPTIC SENSORS

[75] Inventor: Wylie I. Lee, Laguna Hills, Calif.

[73] Assignee: Ohmeda Inc., Liberty Corner, N.J.

[21] Appl. No.: 106,247

[22] Filed: Aug. 13, 1993

[51] Int. Cl.⁵ .............................. A61B 5/00
[52] U.S. Cl. ................... 128/634; 356/243; 356/41
[58] Field of Search ............. 128/633–634, 128/664–667; 356/41, 243, 39–40; 73/1 G

[56] References Cited

U.S. PATENT DOCUMENTS

| | | |
|---|---|---|
| 4,050,450 | 9/1977 | Polanyl et al. |
| 4,322,164 | 3/1982 | Shaw et al. |
| 4,650,327 | 3/1987 | Ogi. |
| 4,744,656 | 5/1988 | Moran et al. |
| 4,796,633 | 1/1989 | Zwirkoski ............... 128/634 |
| 4,823,167 | 4/1989 | Manska et al. ........... 128/634 X |
| 4,981,355 | 1/1991 | Higgins .................. 128/634 X |

*Primary Examiner*—Angela D. Sykes
*Attorney, Agent, or Firm*—Roger M. Rathbun; Larry R. Cassett

[57] ABSTRACT

A calibration boot for use with an optical catheter includes a plurality of materials, each having a different reflectivity characteristic with respect to known wavelengths of light. The boot is positioned over the distal end of the optical catheter and light is emitted from the distal end of the optical catheter into one of the materials at a time. At each emission, the reflected or backscattered light is measured by a detector and a plurality of signals are obtained. The plurality of readings are used to calibrate the overall optical catheter and system. The use of a plurality of calibration signals improves the overall system accuracy, particularly where two or more variables are present in the measured parameter. In the preferred system, the parameter being sensed in the oxygenatin of blood invasively.

19 Claims, 3 Drawing Sheets

DISPOSABLE CALIBRATION BOOT FOR MULTI-POINT CALIBRATION IN FIBER OPTIC SENSORS

BACKGROUND OF THE INVENTION

This invention relates to fiber optic sensors that may be incorporated on the end of a catheter to measure a blood parameter such as oxygen saturation, hematocrit or other parameter and, more particularly, to a disposable calibrator that offers multipoint calibration in a single package.

It has been well recognized that a fiber optic sensor requires calibration to compensate for manufacturing variations such as the light transmission of fibers, spacing between fibers at the tip of the sensor etc. There are also variations in the instrumentation such as the light output, the gain of the receiving circuit having the photodetectors, and the loss in the connection between the instrument and the fiber optic sensor. The calibration of the whole system requires a reference material that will provide a known amount of signal when the sensor is in close contact with the reference material. The algorithm within the signal processing in the instrument will generate a set of correction factors such that the instrument indicates the known value that is associated with the reference material.

Current known means of providing such calibration are as shown and described in U.S. Pat. No. 4,322,164 of Shaw et al and U.S. Pat. No. 4,744,656 of Moran et al. In each of the aforementioned patents, however, the calibration utilizes one substance to provide a known amount of signal and thus calibration is accomplished by selecting only one point on a calibration curve.

If the optical signal such as reflection light, scattered light, fluorescent light, is linearly proportional to the change of one physical parameter, such as the oxygen content of the blood, then one point calibration is sufficient for the required accuracy. However, if the signal is a function of more that one physical parameter, for example, the reflection light changes as the oxygen content and the hematocrit of the blood changes, then the system accuracy is not sufficient with one point calibration but requires two point or multi point calibration.

Accordingly, in such instances, the systems of the aforementioned patents are not sufficient to provide the accuracy for the measurement of blood parameters.

SUMMARY OF THE INVENTION

The present invention provides a means and method of calibrating a fiber optic sensor having improved accuracy and capable of locating multiple points along a calibration curve.

In the present invention, a calibration boot is employed and which contains more than one calibration substance, preferably two such substances and therefore the calibration of the optical fiber, combined with the instrumentation, may be used where the relationship of the parameter being measured is based on a linear relationship or a relationship wherein more than one variable is present.

In the preferred embodiment of the subject invention, a calibration boot is provided and which fits over the distal end of a catheter having fiber optic sensors. The boot contains two materials that have known characteristics of, for example, reflection and the optical fibers therefore can transmit light radiation and receive that reflected light radiation and use the returned radiation from both of the materials to establish a calibration curve for the overall catheter and instrument. The two substances are employed separately with the one substance first used to establish one point on a calibration curve and then the second substance is used in a like manner to establish a second reflected signal and thus a second point on the calibration curve.

Accordingly, in use, the distal end of the optic fibers is initially in contact with one of the substances and then, after taking a reading, the ends of the optical fibers are then displaced and are repositioned so as to contact the other substance and use it to obtain the second point of reference for the calibration curve.

DESCRIPTION OF THE PREFERRED EMBODIMENT

Figure 1:
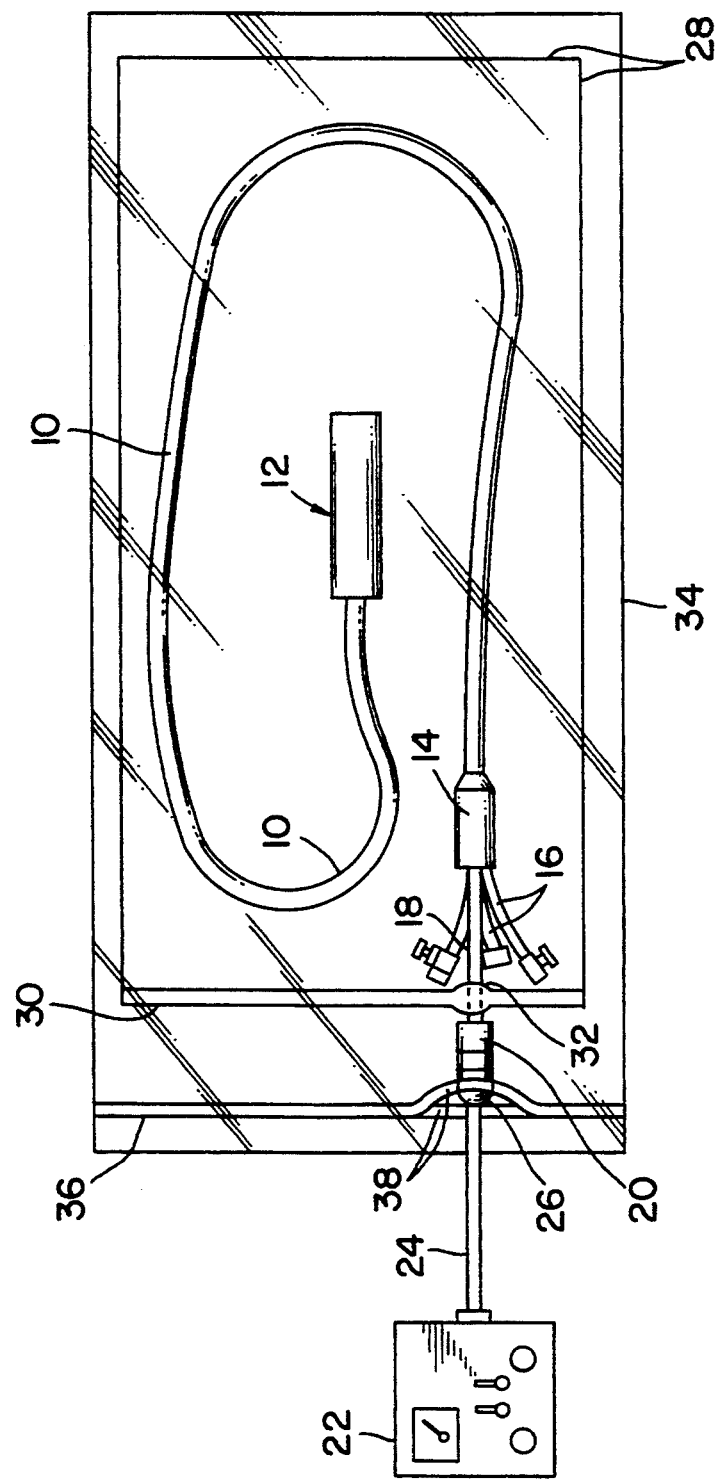
FIG. 1 is a schematic view of an optical catheter on which the subject invention is used and is disposed within its shipping container.

Referring now to FIG. 1, there is shown a schematic view of an optical catheter 10 having affixed to the distal end thereof a calibration boot 12, the purpose of which will be later explained.

At the proximal end of the optical catheter 10, there is a connector manifold 14 and extending proximally from connector manifold 14 are a plurality of individual tubes and electrical extensions 16 and including , in particular, a fiber optic extension 18 ending in a fiber optic connector termination 20. In use, the various tube and electrical extensions 16 are connected, during use, to respective external devices for injecting or withdrawing fluids and for transmission of electrical signals.

As to the fiber optic extension 18, its use is to transmit optical signals to and from the fiber optic connector termination 20 and the distal end of the optical catheter 10. An electronic instrument 22, as shown, is used to provide those optical signals to fiber optic connector termination 20 by means of an optical signal transmission means 24 and which is coupled to the fiber optic connector termination 20 by a connector 26. The electronic instrument 22 also receives optical signals from the distal end of the optical catheter 10 for interpreting the information embodied in those signals. Such information typically includes the characteristic of a body fluid, such as blood, and may include chemical characteristics such as hematocrit, blood oxygen saturation or other blood parameter.

Advantageously, the optical catheter 10 is sterilized and is contained for shipment within a sterile transparent bag 28 whose mouth is sealed by heat or otherwise along a marginal area 30. Preferably, this marginal area 30 is sealed around the optical signal transmission means 24 just distal to the fiber optic connector termination 20, thus permitting passage of optical signals between the electronic instrument 22 and the distal end of the optical catheter 10 while maintaining a sterile barrier 32 around the protruding fiber optic extension 18.

The sterile transparent bag 28 and protruding fiber optic extension 18 and fiber optic connector termination 20 are preferably enclosed in a larger bag 34, which may have a readily and repetitively openable and closable dust closure 36 which may be of the "snap locking" type.

In particular, the closure 36 is advantageously of a type that can be opened only partially in a particular area, such as shown at 38. Such an arrangement allows functional interconnection of the optical fiber connector 26 and fiber optic connector termination 20 with minimal environmental exposure of the area near the sterility barrier at the marginal area 30 of the inner transparent bag 28.

With suitable clean room techniques, calibration can thus be checked any number of times without compromising the ultimate sterility of the optical catheter 10. As indicated, calibration is accomplished by the sending of an optical signal from the electronic instrument 22 to the distal end of the optical catheter 10 where it is reflected within the calibration boot 12 by a material having a known reflectivity and the reflected optical signal s transmitted to the electronic instrument 22 where it is used to establish a point on a calibration curve.

As will be seen with the present invention, calibration boot 12 contains two materials having known reflectivity with respect to the emitted optical signal from the distal end of optical catheter 10. Since the two materials must, of course, have differing reflectivities with respect to the exciting signal, one of the materials may be that conventionally used, that is, a homogeneous suspension of titanium particles scattered in silicon. The other material may also be scattered titanium particles embedded in silicon but also has one or more dyes added to alter its backscatter characteristics to a desired amount in order to evolve the second point for a calibration curve.

Each reflected or backscattered calibration signal, of course, establishes one point on the calibration curve and an algorithm thus completes the calibration curve for the later transmission and reflection of multiple points during the end use of the optical catheter 10 to read the various desired blood parameters.

As also may be seen from the foregoing description, the calibration boot 12 may be handled and moved with respect to the optical catheter 10 without disturbing the sterility and the use of such movement will be later explained.

Figure 2:
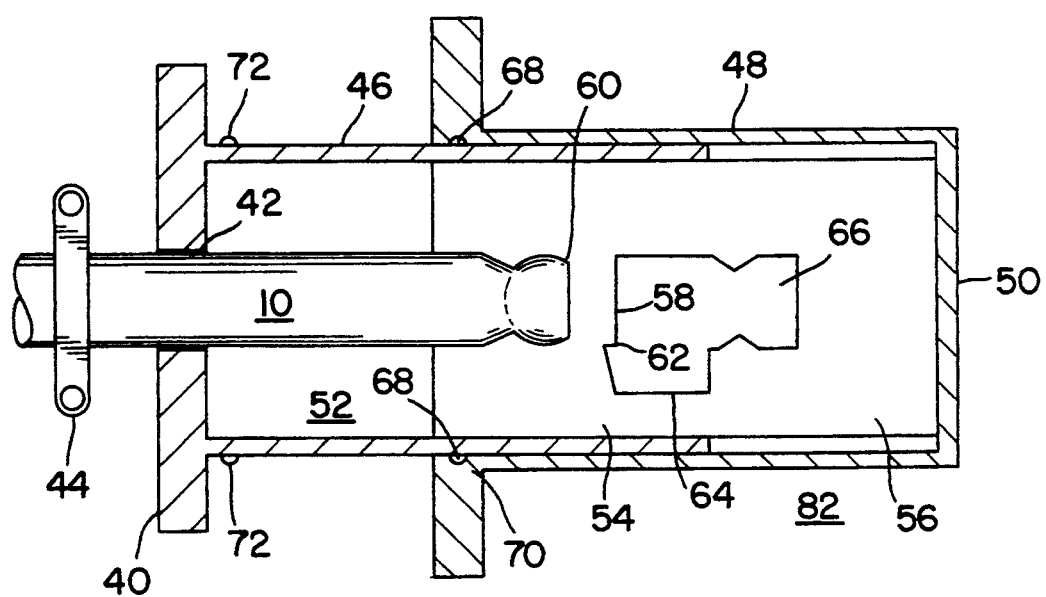
FIG. 2 is a side cross-sectional view of a two point calibration boot constructed in accordance with the present invention.

Turning now to FIG. 2, there is shown a side cross-sectional view of a calibration boot 12 constructed in accordance with the present invention. As shown, the calibration boot 12 has a flange 40 at its proximal end and which flange has an opening 42 through which is closely fitted the optical catheter 10. The optical catheter 10 is secured in its tray or shipping container by means of a strap 44 which may be of an elastic or ribbon material.

Depending outwardly distally from the flange 40 is a hollow cylindrical projection 46 that covers and contains the distal end of the optical catheter 10. A sleeve 48 is fitted over the distal end of the hollow cylindrical projection 46 and is closed at its distal end 50. As shown, therefore, the combination of the hollow cylindrical projection 46 and the sleeve 48 serve to form a cavity 52 within the calibration boot 12 completely enclosing the distal end of the optical catheter 10. Both components of the calibration boot 12 are preferably made of an easily injected molded material that is substantially opaque to shield the distal end of the optical catheter 10 from ambient or extraneous light.

Within the cavity 52 are formed first and second compartments 54 and 56, respectively, and each of which contain a different calibration material. Taking the first compartment 54, the material surrounds and conforms to the distal end of the optical catheter 10 such that a light signal emanating from the distal end will be reflected from the material in first compartment 54 back into the optical catheter 10 and thence back as shown in FIG. 1 to the electronic instrument 22 as a calibration signal.

The second compartment 56, contained essentially within the sleeve 48 contains a second material having a different reflection characteristic and thus will provide a different light reflection signal to the electronic instrument 22 to be used as a second calibration signal.

As also can be noted in FIG. 2, a removable wall 58 is formed in the material contained within the first compartment 54 just distally with respect to the distal end of the optical catheter 10 and generally along its axis. By removable, it is intended to mean that the removable wall 58 may be broken away or in some manner removed from its position as a barrier between the material within the first compartment 54 and the material within the second compartment 56 with respect to the distal end of the optical catheter 10.

In the embodiment of FIG. 2, a notch 60 is formed substantially around the removable wall 58 such that a living hinge 62 is formed. As the sleeve 48 is moved longitudinally inwardly, that is, toward the proximal end of the optical catheter 10, the distal end of the optical catheter 10 is pressed against the removable wall 58, causing it to break away from its position and the living hinge 62 allows the removable wall 58 to pivot around the living hinge 62 to be displaced into the recess 64. Further movement of the sleeve 48 causes the distal end of the optical catheter 10 to move further longitudinally until it enters the indentation 66 formed in the material in the second compartment 56. The indentation 66 is shaped to fit over and enclose the distal end of optical catheter 10, and a second calibration signal may be obtained, this time using the reflection characteristics of the material within the second compartment 56.

The removable wall 58 therefore needs to be relatively thin in order to allow easy rupture of the material. With the use of a silicon material, it has been found that the thickness of the removable wall 58 should be less than 5.0 min. and preferably about 4.0 mm.

The sleeve 48 may also have a means to retain it in its positions on hollow cylindrical projection 46, such as one or more male detents 68 formed on the outer surface of the hollow cylindrical projection 46 and which fit within female detents 70 formed on the inside surface of the sleeve 48. As the sleeve 48 is moved to allow the optical catheter 10 to enter the second compartment 56, the female detents 70 realign with another set of one or more male detents 72 to hold the sleeve 48 in position when the second calibration point is being obtained.

As may now be seen, in summary, the calibration boot 12 allows the taking of two calibration readings using two different materials, each having known, but different reflectivity to the light radiation emitted from the distal end of the optical catheter 10. A first calibration signal is obtained when the distal end of optical catheter 10 is surrounded by a material in the first compartment 54. The positions of the distal end of the optical catheter and the calibration boot 12 are then changed such that the distal end of the optical catheter 10 becomes adjacent and abutting against the material in the second compartment 56 where a second calibration signal can be obtained based on the different, but known, reflectivity of the different material within the second compartment 56.

Figure 3:
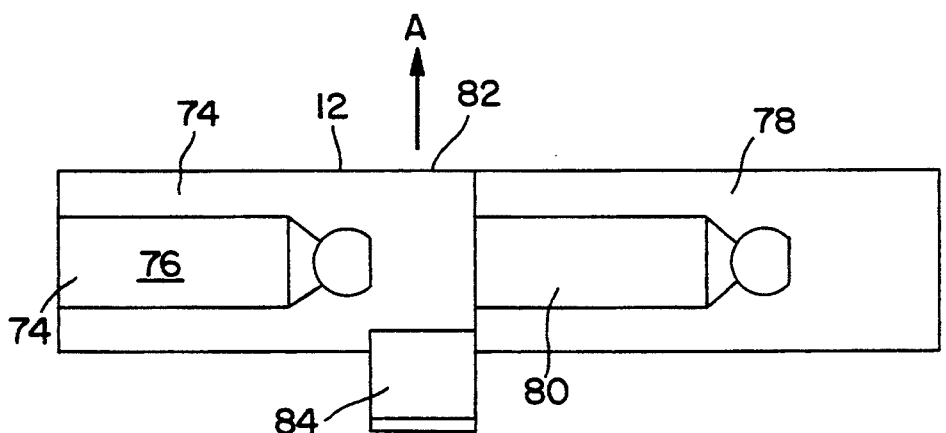
FIG. 3 is a side cross-sectional view of an alternate embodiment of a two point calibration boot constructed in accordance with the present invention.

Turning now to FIG. 3, there is shown a side cross-sectional view of an alternate embodiment of a calibration boot constructed in accordance with the principles of this invention. In this embodiment, the calibration boot 12 comprises a first cavity 74 having an opening 76 conformed to the shape of the distal end of the optical catheter 10 and a second cavity 78 also having an opening 80 so shaped. As noted, the first cavity 74 is formed within material having a known reflectivity and the second cavity 78 is formed within a material of another known reflection characteristic. Thus, the first and second cavities, 74 and 78 are formed within compartments that are separate.

A slide 82 is positioned between the first cavity 74 and the second cavity 78 and is movable between a first position as shown in FIG. 3 and a second position (not shown) in which the slide 82 is moved in the direction of arrow A to a position where an open hole 84 is aligned with the distal end of the optical catheter 10. When the slide 82 such that the optical catheter 10 may enter into the second cavity 78, or compartment, and lodge itself within opening 80 where the second calibration signal may be generated.

Slide 82, when in its first position, is made of the same material as surrounding the first cavity 74 so that the first calibration signal may be generated while in such first position. After obtaining such first calibration signal, obviously, the slide 82 is moved to its position where the cavity 74 is aligned with the optical catheter and the optical catheter then moved longitudinally so that it is inserted into the second cavity 78 where a second calibration signal may be obtained through the backscatter from the second material. Accordingly, again, two separate and different calibration signals are obtainable from the calibration boot 12.

Figure 4:
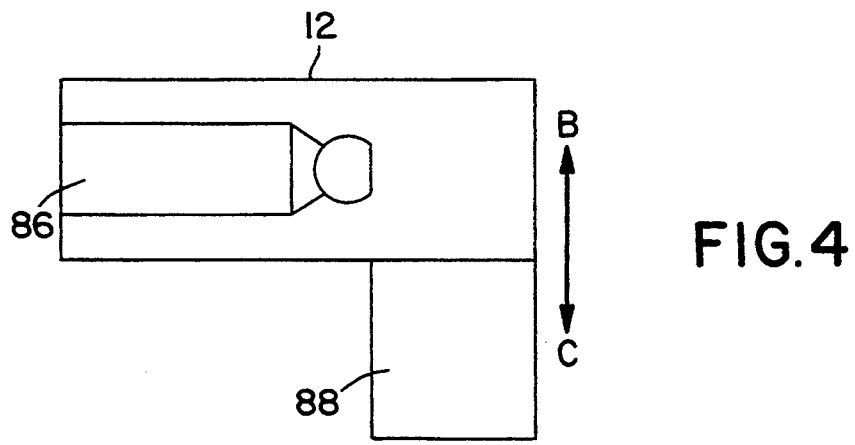
FIG. 4 is a side cross-sectional view of yet a further embodiment of the calibration boot constructed in accordance with the present invention.

In FIG. 4, there is shown a side cross-sectional view of yet another embodiment of the subject invention. In this embodiment, the calibration boot 12 is comprised of one material having a known reflectance characteristic and having a cavity 86 formed therein configured to match the external dimensions and configuration of the optical catheter. A slide 88 is located distal to and abutting against the internal end of the cavity 86 and therefore would abut against the end of an optical catheter positioned within the calibration boot 12. The slide 88 is constructed of two sections, each made of a material having a known reflectance characteristic. In the position as shown in FIG. 4, the material that would produce the calibration signal is the same material as that comprising the calibration boot 12. When the slide 88 is moved to a position in the direction of the arrow B, the second material now is located at the internal end of the cavity 86 and therefore that material would produce the calibration signal from an optical catheter positioned within the calibration boot 12.

As can be seen, the slide 88 can be alternated between its two positions by moving it either in the direction of arrow B or back to its position as in the FIG. 4 by moving it in the direction of the arrow C. Thus the two calibration signals produced by reflection from the two different materials may be selected and, in each case, a separate calibration signal is obtained in order to provide two points of calibration for the algorithm.

Figure 5:
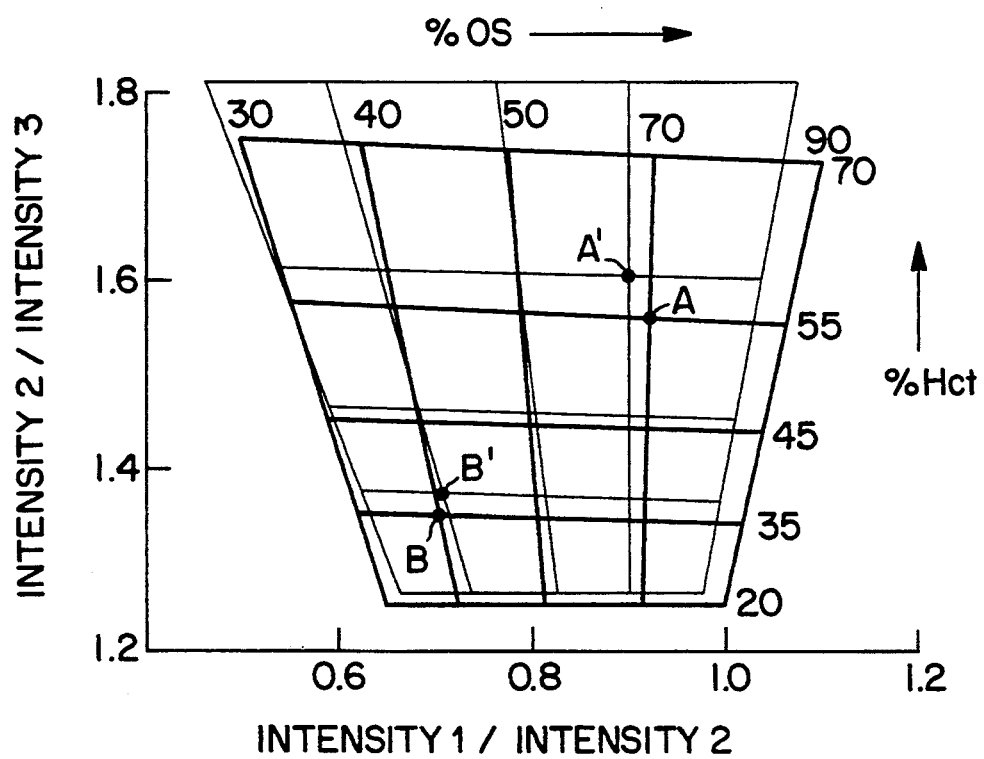
FIG. 5 is a series of curves representative of a typical calibration algorithm curve for the present invention and a curve representative of optical catheter system that is out of design specifications.

Finally, in FIG. 5, there is shown a depiction of calibration curves typical of an optical catheter that measures blood oxygenation. The curves are calibration curves for a system measuring the intensities of three optical means and having an algorithm for measuring more than two parameters. In FIG. 5, there is shown as the vertical scale, the ratio of the intensities of the backscattered radiation from two of the optical means. The ratio of the detected intensities of the backscattered radiation is thus plotted. Similarly, the horizontal scale represents the ratio of backscatter resulting from emitted light of one of the optical means used to obtain the ratio of the vertical scale along with the backscatter intensity resulting from a third optical means. The three optical means system may be as described in U.S. Pat. No. 4,114,604 in the name of Shaw et al., or the Moran U.S. Pat. No. 4,776,340 or other system utilizing a plurality of optical means.

The solid grid of FIG. 5 shows the correct calibration algorithm with the percent of blood oxygen saturation increasing to the right and the percent of hematocrit increasing with vertical height. The graph therefore is a typical two dimensional graph for the measurement of two parameters, in this case, percent oxygen saturation and percent of hematocrit of blood.

The dotted line grid represents a typical depiction where the sensor is out of design specification, that is, possibly one or more of the wavelengths are off spec, or there is some other defect in the system. On the solid line curve, the desired calibration points are shown as points A and B while the actual response from the off-spec system is shown as A' and B'.

Thus the calibration is used to bring the dotted line curve back to the solid line position. When only one variable is detected, the dotted curve is readily simply scaled and the entire dotted curve is moved to the position of the solid line curve. With two parameters, however, the dotted line curve not only requires scaling from the solid line position, but it is additionally rotated and it therefore also needs rotation as well as scaling to clear up the distortion to fully position the dotted line curve to the desired position of the solid curve.

Accordingly, by tile use of two calibration points, not only can the dotted line curve be scaled back to assume the solid line position, but with the use of the second calibration point, the distortion in the curve can be corrected and the curve rotated to the correct position so that the off spec instrument may assume the solid line position for the algorithm. Thus, with the two point calibration system as disclosed, a two parameter sensor can be accurately calibrated by not only scaling the detected curve to the correct position but the detected curve may also be rotatedr so that it more accurately positions itself upon the correct curve, that shown in the solid line of FIG. 5.

As numerous variations and combinations of the features above can be utilized without departing from the present invention, the foregoing description of the preferred embodiments should be taken by way of illustrat-

I claim:

1. A disposable calibration boot for an optical catheter having a distal end and having at least one optical means for emitting light radiation from the distal end and at least one optical means for receiving light radiation at the distal end, said disposable boot comprising:
   a body,
   a cavity defined in said body to receive the distal end of the optical catheter, said body shielding the distal end of the catheter from ambient light when the distal end is positioned within said cavity;
   said body having a plurality of isolated compartments, each of said plurality of compartments containing a material having a known reflectivity to return a signal into the receiving optical means upon transmission of a known radiation from the emitting optical means,
   said body adapted to be positioned on the end of the optical catheter and being movable with respect thereto to position the distal end of the optical catheter adjacent each of said plurality of materials within said body such that the emitting and receiving optical means of the optical catheter selectively interacts individually with each of said plurality of materials to obtain separate backscattered signals from each of said plurality of materials within said calibration boot from light radiation caused to be emitted from the optical means of the optical catheter.

2. A disposable calibration boot as defined in claim 1 wherein said plurality of compartments is two.

3. A disposable calibration boot as defined in claim 2 wherein said plurality of isolated compartments are separated by a thin, removable material isolating said compartments.

4. A disposable calibration boot as defined in claim 3 wherein said thin, removable material is a polymeric material having a thickness of less than about 5.00 mm.

5. A disposable calibration boot as defined in claim 3 wherein said body is movable longitudinally along the catheter, thereby causing the distal end of the catheter to break said thin, removable material to allow the distal end of the catheter to interact with each of said plurality of materials on either side of said removable material.

6. A disposable calibration boot as defined in claim 5 wherein one of said materials comprises a polymer having a known reflectivity and the other of said materials comprises a polymer having a dye to modify its reflectivity.

7. A disposable calibration boot as defined in claim 2 wherein said body includes a slide having a first and a second material, said slide being movable between a first position wherein the distal end of the optical catheter is positioned adjacent the first material and a second position wherein the distal end is adjacent the second material.

8. A disposable calibration boot as defined in claim 2 wherein said body includes a slide comprised of a first material, said slide being movable between a first position wherein the distal end of the optical catheter is adjacent a first material and a second position wherein said calibration boot is movable longitudinally along the optical catheter to cause the optical catheter to further enter said calibration boot to a position adjacent a second material.

9. An optical catheter having a disposable calibration boot, said optical catheter having a distal end and having an optical fiber means for emitting light radiation from said distal end and an optical fiber means for receiving light radiation at said distal end, said disposable boot comprising a body secured to said distal end of said optical catheter and having a cavity defined in said body surrounding said distal end of said optical catheter and shielding said distal end from ambient light, a first material contained within said body and having a known reflectivity to reflect a signal into said receiving optical fiber means upon transmission of a known radiation from said emitting optical fiber means, a second material contained within said body and having a different known reflectivity to reflect a second signal into said receiving optical fiber means upon transmission of the known radiation from said the emitting optical fiber means; and means to separately and individually position said distal end of said optical catheter to a position adjacent each of said plurality of materials within said calibration boot to cause said emitting and receiving optical means to initially interact with each of said materials to obtain a plurality of calibration signals from said calibration boot.

10. An optical catheter having a disposable calibration boot as defined in claim 9 wherein said calibration boot further comprises a thin removable material separating said first material from said second material, said thin material adapted to be removed by the longitudinal movement of said distal end of said optical catheter whereby said distal end of said optical catheter may be moved from a position interacting with said first material to a position interacting with said second material.

11. A an optical catheter having a disposable calibration boot as defined in claim 10 wherein said thin removable material is a polymeric material having a thickness of less than about 5.00 mm.

12. An optical catheter having a disposable calibration boot as defined in claim 11 wherein said thin removable material has a thickness of about 4.00 mm.

13. An optical catheter having a disposable calibration boot as defined in claim 9 wherein said means to separately and individually position said distal end of said optical catheter comprises a slide operable within said calibration boot and constructed of said first and said second material, said slide being movable between a first position wherein said first material is positioned adjacent said distal end of said optical catheter and a second position wherein said second material is positioned adjacent said distal end of said optical catheter, whereby said emitting and said receiving optical means can selectively interact separately with said first and said second material.

14. An optical catheter having a disposable calibration boot as defined in claim 9 wherein said means to separately and individually position said distal end of said optical catheter comprises said calibration boot having a distal end made of said first material, a slide operable within said calibration boot and comprised of said second material and having an opening, said slide being movable between a first position wherein said distal end of said optical catheter is adjacent said second material of said slide and a second position wherein said distal end of said optical catheter is movable longitudinally through said opening in said slide to a position adjacent said first material in said distal end of said calibration boot.

15. A method of providing two point calibration signals from an optical catheter having a distal end, such catheter having an optical means for emitting light radiation to said distal end and a receiving optical means for receiving light radiation at the distal end, said method comprising the steps of:

fitting a disposable boot comprised of two isolated materials, each having differing properties of reflectivity to light radiation over the end of an optical catheter, positioning the catheter within said disposable boot such that the distal end of the catheter is located adjacent of the two materials, causing light radiation to be emitted from the distal end of the catheter from the emitting optical means into the one of the two materials and detecting a first signal received back into the distal end through the receiving optical means, repositioning the catheter within said disposable boot such that the distal end of the catheter is located adjacent the other of the two materials, causing light radiation to be emitted from the distal end of the catheter from the emitting optical means into the other of the two materials and detecting a second signal received back into the distal end through the receiving optical means, and calibrating the optical catheter and the detecting means based upon the first and second signals.

16. A method of calibrating an optical catheter as defined in claim 15 wherein the materials are separated by a removable wall and the said step of repositioning the distal end of the catheter comprises the step of causing the distal end of the optical catheter to break the removable wall and moving the distal end longitudinally to a position adjacent the second material.

17. A method of calibrating an optical catheter as defined in claim 16 wherein the thin removable wall is comprised of the first material of a polymeric material having a thickness of less than about 5.00 min.

18. A method of calibrating an optical catheter as defined in claim 15 wherein the disposable boot includes a slide made of the two materials and the step of positioning the catheter comprises positioning the catheter such that the distal end is adjacent one of the two materials of the slide and the step of repositioning the catheter comprises moving the slide with respect to the catheter such that the distal end of the catheter is adjacent the other material of the slide.

19. A method of calibrating an optical catheter as defined in claim 15 wherein the disposable boot includes a slide made of one of the two materials and has an aperture, and the step of positioning the catheter comprises positioning the catheter such that the distal end is adjacent the one material of the slide and the step of repositioning the catheter comprises moving the slide to a position wherein the distal end of the catheter is aligned with the aperture and moving the distal end of the catheter longitudinally through the aperture to be repositioned adjacent the other material.

* * * * *